(12) United States Patent
Devisetty et al.

(10) Patent No.: US 8,334,002 B2
(45) Date of Patent: Dec. 18, 2012

(54) CINNAMALDEHYDE—ALLICIN COMPOSITIONS AND THEIR METHOD OF USE

(75) Inventors: Bala N. Devisetty, Buffalo Grove, IL (US); Bassam Shammo, Mundelein, IL (US); Linda A. Rehberger, Glenview, IL (US); Rebecca Dickenson, Volo, IL (US); Heemanshubhai K. Patel, Des Plaines, IL (US); Daniel F. Heiman, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 257 days.

(21) Appl. No.: 12/580,401

(22) Filed: Oct. 16, 2009

(65) Prior Publication Data

US 2010/0099777 A1  Apr. 22, 2010

Related U.S. Application Data

(60) Provisional application No. 61/106,191, filed on Oct. 17, 2008.

(51) Int. Cl.
*A01N 65/00* (2009.01)
*A61K 36/54* (2006.01)

(52) U.S. Cl. .................................. 424/739; 424/754

(58) Field of Classification Search .................. None
See application file for complete search history.

(56) References Cited

U.S. PATENT DOCUMENTS

| 4,546,108 | A | * | 10/1985 | Rout et al. ................... 514/464 |
| 4,978,686 | A | * | 12/1990 | Sotome ......................... 514/698 |
| 5,051,255 | A | | 9/1991 | Devidas et al. |
| 5,057,141 | A | | 10/1991 | Rodriquez-Kabana et al. |
| 5,182,207 | A | | 1/1993 | Ward et al. |
| 5,360,607 | A | | 11/1994 | Eyal et al. |
| 5,439,934 | A | | 8/1995 | Wood et al. |
| 6,231,865 | B1 | | 5/2001 | Hsu et al. |
| 6,251,951 | B1 | | 6/2001 | Emerson et al. |
| 6,750,256 | B1 | | 6/2004 | Crandall, Jr. et al. |
| 2004/0077713 | A1 | * | 4/2004 | Maupin et al. ................ 514/475 |
| 2006/0110472 | A1 | * | 5/2006 | Miron et al. .................. 424/754 |

FOREIGN PATENT DOCUMENTS

WO  WO 2006/109028  10/2006

OTHER PUBLICATIONS

Miller (Journal of Nematology, 11(4):402-403, 1979).*
Y.Oka, "Nematicidal activity of essential oil components against the root-knot nematode Meloidogyne javanica", Nematology, 2001, vol. 3(2), pp. 159-164.
R. Pandy et al., "Essential oils as potent sources of nematicidal compounds", J. Phytopathology 148, 2000, pp. 501-502.
Park Nematicidal activity of plant essential oils and components from garlic (*Allium sativum*) and cinnamon (*Cinnamomum verum*) oils against the pine wood nematode (*Bursaphelenchus xylophilus*), 2005 Nematology vol. 7(5) pp. 767-774.
Auger et al., "Insecticidal and fungicidal potential of Allium substances as biofumigants", Argroindustria 2004, vol. 3 No. 3, pp. 5-8.
Lawson et al., "Compositions, Stability, and Bioavailability of Garlic Products Used in a Clinical Trial" Journal of Agricultural Food Chemistry, 2005, 53, pp. 6254-6261.
Fujisawa et al., "Biological and Chemical Stability of Garlic-Derived Allicin", Journal of Agricultural and Food Chemistry, 2008, 56, pp. 4229-4235.

* cited by examiner

*Primary Examiner* — Bong-Sook Baek
(74) *Attorney, Agent, or Firm* — Wood, Phillips, Katz, Clark & Mortimer

(57) ABSTRACT

The invention generally relates to mixtures of cinnamaldehyde (cinnamic aldehyde) and allicin (10%) in emulsifiable suspension formulations at ratios ranging from 1:1 to 20:1 for protecting plants from damage by nematodes, fungal pathogens, insects and mites. The nematicidal compositions described are easily flowable, easily mixable in water and have low volatility and exhibit no phytotoxicity. Methods of applying the compositions for agriculture use are disclosed.

9 Claims, No Drawings

CINNAMALDEHYDE—ALLICIN COMPOSITIONS AND THEIR METHOD OF USE

FIELD OF THE INVENTION

The present invention generally relates to cinnamaldehyde—allicin compositions that have synergistic activity against plant parasitic nematodes and other soil and plant pathogens or insects, including termites or mites, and their methods of use.

BACKGROUND OF THE INVENTION

Plant parasitic nematodes cause serious economic damage to many agricultural crops around the world. The nematodes in this group are microscopic worms and in general are obligate parasites of plants. They feed mostly on the roots of host plants; however, several genera are known to parasitize above-ground parts including stems, leaves and flowers as well.

Almost all the plant species of economic importance are susceptible to infection by some species of nematodes (notable exceptions are marigolds and asparagus). For example, root knot nematodes (RKN), (*Meloidogyne* spp.) are capable of parasitizing more than 3,000 species of crop plants. These plants include agronomic crops, vegetable crops, fruit trees, flowering trees and shrubs. Nematodes reportedly cause crop losses worth more than six billion dollars in the United States alone and more than one hundred billion dollars around the world.

The symptoms due to parasitic nematode injury vary widely depending on the plant host, the nematode species, the age of the plant, the geographical location and climatic and external environmental conditions. In general, an overall patchy appearance of plants in a field is considered to be indicative of nematode infestation. More specifically, nematode injury results in galling of the roots (abnormal swelling in the tissue due to rapid multiplication of cells in the cortical region) caused by species of root knot (*Meloidogyne* spp.) and cyst (*Heterodera* spp.) nematodes, lesions (localized, discolored areas) caused by lesion nematodes (*Pratylenchus* spp.), suppression of cell division resulting in stubby roots (*Trichodorus* spp.), growth abnormalities including crinkling or twisting of above-ground parts (*Aphelenchoides* spp.), and even cell necrosis (death) in some cases. Plant parasitic nematodes may be endoparasitic in nature, as in the case of the root knot and lesion nematodes, or ectoparasitic as in the dagger nematode (*Xiphinema* spp.) and lance nematode (*Hoplolaimus* spp.). Nematodes can be vectors of plant viruses and are also known to induce disease complexes, predisposing plants to infection by other plant pathogenic fungi and bacteria.

Chemical nematicides, either soil fumigants or non-fumigants, have been in use for many years and are among the few feasible options for countering nematodes. At present, repeated applications of synthetic chemicals to the field are required prior to planting the crop. These chemicals are extremely toxic to non-target organisms besides nematodes and many of them may pose serious threats to the environment. With the emphasis on clean water and air by environmental groups and governmental agencies and the detection of many of these active ingredients or the metabolites thereof in ground water and several non-target organisms, there has been serious concern as to the wisdom of continuing the use of these chemicals. One of the most effective, economical, and widely used nematicides, DBCP (1,2-dibromo-3-chloropropane), found in ground water has been judged to induce male sterility and possible carcinogenesis. Another widely used chemical, EDB (ethylene dibromide), has also been found in ground water.

Another very common insecticide-nematicide, aldicarb (2-methyl-2-(methylthio)-propionaldehyde-o-(methylcarbamoyl)oxime), has been found to have high acute toxicity. Aldicarb has been found in ground water in several regions of United States. 1,3-D (1,3-dichlorpropene), yet another commonly used soil fumigant and nematicide, is identified as a probable carcinogen. The US EPA recently revoked all tolerances for residues of carbofuran (2,3-dihydro-2,2-dimethyl-7-benzofuranyl methylcarbamate) on crops and cancelled some product registrations after determining that the risk from aggregate exposure does not meet their safety standard. The recent decision by the EPA to limit and eventually discontinue the use of the soil fumigant, methyl bromide, for agricultural purposes, including it's effect as a nematicide, presents a threat to the efficiency and quality of agricultural production in the United States.

Natural products such as N-acetyl-D-glucosamine, which may be derived from microorganisms and which are the waste products of industrial fermentation processes, have been disclosed as nematicidal in U.S. Pat. No. 5,057,141.

Biopesticides have been developed as an alternative to chemical pesticides. They are obtained by fermentation and can be used either as a crude biomass or purified. Typically, fermentation is carried out at temperatures in the range of 20-40° C. For example, submerged fermentation at 28-30° C. of *Paecilomyces fumosoroues* fungal isolate ATCC No. 20874 produces a fungal biomass for control of nematode infestation as disclosed in U.S. Pat. No. 5,360,607; whole fermentation broth from fermentation at 28° C. of *Streptomyces thermoarchaensis* NCIB 12015 is disclosed as nematocidal in U.S. Pat. No. 5,182,207; broth obtained from fermentation of *Streptomyces cyaneogriseus noncyanogenus* NRRL 15773 at 28° C. is effective against nematodes as disclosed in U.S. Pat. No. 5,439,934; and broth obtained by fermentation of the fungus *Myrothecium verrucaria* at temperatures 25 to 30° C. is disclosed as nematicidal in U.S. Pat. No. 5,051,255.

However, there is still a need for the development of new and effective nematicides. Plants were suggested as a source of effective pesticidal compounds as many plant essential oils exhibit antimicrobial, insecticidal, fungicidal and herbicidal activity. They have been applied as pesticides for pest, disease and weed management.

Certain plant essential oils have been evaluated by the USEPA and have been determined to qualify for an exemption from registration as minimum risk pesticides and are listed in 40 C.F.R. §152.25 (b). However, high volatility, phytotoxicity and low water solubility of some oils have limited their use in crop protection.

One plant essential oil used in agricultural applications is ProGuard® 30% Cinnamaldehyde Flowable Insecticide, Miticide and Fungicide (U.S. Pat. Nos. 6,750,256 B1 and 6,251,951 B1). However, a disadvantage of this commercial product is that it contains the chemical preservative o-phenylphenol.

Nematicidal activity of plant essential oils was reported, among others, by Y. Oka (Nematology, Vol. 3(2), pp. 159-164, 2001) and R. Pandey (J. Phytopathology 148, 501-502 (2000)). Essential oils of some plants and their components have been tested for nematicidal activity in vitro and in soil. Some plant essential oils, which were determined to have nematicidal activity, include essential oils of apple mint (*Mentha rotundifolia*), caraway (*Carum carvi*), fennel (*Foeniculum vulgare*), oregano (*Origanum vulgare*), Syrian oregano (*Origanum syriacum*), and wild thyme (*Coridothy-*

*mus capitatus*). Also, it was reported that aromatic and aliphatic aldehydes, including cinnamic aldehyde (also known as cinnamaldehyde) possess strong nematicidal activity in vitro. For example, U.S. Pat. No. 6,251,951 B1 demonstrates that cinnamaldehyde has nematicidal activity in the presence of a 2% Tween 80 and 6% $NaHCO_3$ vehicle.

U.S. Pat. No. 6,231,865 B1 describes a synergistic effect when garlic oil or extract is combined with essential oils, which results in an improved insecticide/fungicide activity. Garlic extract is defined in this patent as any liquid removed from cloves of garlic and may include garlic oil and water. The preferred essential oil in the mixture was claimed to be cottonseed oil, and/or cinnamon oil. Sodium lauryl sulfate was used at 10% to emulsify the garlic extract. No attempt was made to describe or quantify the actual composition of garlic juice. Constituents in the garlic juice may vary substantially depending upon the source of garlic and method of extraction. Nematicidal activity with the garlic juice is, however, not described.

WO/2006/109028 "A Pesticide and Repellent" describes the use of garlic liquid concentrate as an insecticide, nematicide and molluscocide. Garlic concentrate was shown to have the properties associated with garlic oil/fresh garlic extract in terms of its repellency to various life forms and its action as a pesticide, but it does not require the distillation stage involved in the isolation of the garlic oil and is stable to long term storage without a decrease in the activity of the material. Allyl poly-sulphides, the active components resulting from decomposition of allicin in the garlic liquid concentrate were shown to be in the range 2 to 4% wt./wt. This published patent application also disclosed that diallyl sulphides of the formula RSR, $RS_2R$, $RS_3R$, and $RS_4R$ account for 66% (±10%) by weight of the total poly-sulphides present. These diallyl sulphides were determined to be present in the approximate ratio of 4-5%; 5-8%; 31-38%, and 19-22% by weight, respectively, of the total poly-sulphides present. The published patent application also disclosed a granular formulation of garlic concentrate impregnated onto wood flour with a binder. The granules (NEMguard) were successfully evaluated as nematicidal.

The nematicidal activity of the cinnamyl acetate component of oil from *Cinnamomum verum* and of diallyl disulphide and diallyl trisulphide from garlic (*Allium sativum*) was reported by Park et al, in 2005 (Nematology 7(5), 2005, 767-774). These were the most active essential oils from 43 plant species tested. The main components of the essential oils with nematicidal activity in the 2005 study were reported by Park et al, in 2002 (J. Pesti. Sci. 6, 2002, 271-278) to have insecticidal or acaricidal activity against five major arthropod pests. Diallyl disulphide and diallyl trisulphide from Allium were reported by Auger et al, (Agroindustria 3(3), 2004, 5-8) as having good activity against soil pathogenic fungi, insects and termites.

While both cinnamaldehyde and garlic extract are known in the literature for their nematicidal, insecticidal, fungicidal and miticidal activity, cinnamaldehyde may result in phytotoxicity to target plants especially when used at nematicidal rates (500 ppm and above). At concentrations of 300 ppm, nematicidal activity is only marginal. While at doses of 300 ppm and above, garlic extract may be effective in controlling nematodes, and exhibits no phytotoxicity, its cost per treated acre may be prohibitive.

Garlic extract used in earlier formulation studies is often aqueous based and the stability of active components in aqueous preparations is not well established. No prior art exists for formulations containing concentrated, dry powdered version of garlic extract (allicin) and cinnamaldehyde for effective and economic control of nematodes, fungal pathogens, insects and mites.

Accordingly, there is a need to develop safe, easy-to-use, cost effective delivery systems, so as to improve the biological effectiveness of plant essential oils/plant extracts, for agricultural applications.

SUMMARY OF THE INVENTION

The present invention generally relates to emulsifiable oil suspension formulations suitable for agricultural use that comprises liquid cinnamaldehyde (also known as cinnamic aldehyde) and allicin in powder form, at least one solvent selected from the group consisting of soybean oil, methyl oleate, ethyl lactate and methyl soyate, other seed oils, an emulsifier, a rheological additive, a polar additive and another non-ionic surfactant.

The invention further relates to methods for protecting a plant from at least one pathogen comprising application, to the locus, soil or seeds of the plant, of an effective amount of the claimed formulations. The phrase "protecting a plant" means controlling the growth of pests and pathogens, which may involve killing the pests and pathogens and/or slowing or arresting their proliferation, or providing a confusing or repellent action so that the pest or pathogen is unable to come into contact with the plant and attack it. Representative pests and pathogens include, but are not limited to, nematodes, fungal pathogens *Pythium, Rhizoctonia, Sclerotinia,* insect pests and other pests.

Excellent control of root knot nematodes is obtained at application rates of these compositions that are substantially reduced compared to those required for each of these active ingredients applied individually. For example, a mixture comprising cinnamaldehyde at 100 to 250 ppm and further comprising 20 to 50 ppm of allicin resulted in greater than 95% of gall reduction on roots than when cinnamaldehyde was applied alone at 300 ppm or allicin applied alone at 300 ppm.

DETAILED DESCRIPTION OF THE INVENTION

It was surprisingly discovered that the abovementioned problems caused by plant parasitic nematodes are solved by the compositions of the present invention that comprise cinnamaldehyde and allicin and related derivatives, in certain ratios, such that the composition is synergistic against nematodes. Several compositions comprising both cinnamaldehyde and allicin have been developed.

In one embodiment, the invention provides a formulation suitable for agricultural use comprising an emulsifiable suspension concentrate, comprising one active ingredient, preferably cinnamaldehyde, dissolved in a low volatility solvent (such as vegetable oil) and a second active ingredient, preferably allicin, as a powder suspended in the oil phase with the aid of a suitable rheological additive and an emulsifier for easy dilution in water and application. The composition of the present invention is more effective, non-phytotoxic and requires less of each active ingredient in the mixture than when either of the active ingredients is used individually.

In another embodiment of this invention, the cinnamaldehyde used is at least 75% pure, but preferably at least 98% pure, and the cinnamaldehyde and allicin may be combined in a suitable solvent/carrier such as vegetable oil at ratios varying from 20:1 to 1:1 wt./wt. cinnamaldehyde:allicin.

In a more preferred embodiment, the desired ratios vary from 5:1 to 20:1 wt./wt. cinnamaldehyde:allicin.

In another preferred embodiment, the desired ratios vary from 10:1 to 20:1 wt./wt. cinnamaldehyde:allicin.

The solvent suitable for the formulation is selected from the group consisting of soybean oil, methyl oleate, ethyl lactate, methyl soyate, and other seed oils. The preferred solvent/carrier is food grade soybean oil. The solvent may range from 30% to 80% wt./wt of the formulation. More preferably, the solvent may range from 30% to 62% wt./wt. The amount of solvent used in the formulation will greatly depend upon the amount of cinnamaldehyde and allicin utilized. The 10% allicin is present in an amount that is in the range from 10% to 50% wt./wt. and more preferably in the range of 20% to 40% wt./wt. The allicin as a percentage of the total active components may range between 0.5% to 15% wt./wt. The concentration of cinnamaldehyde in the formulation may range from 2% to 50% wt./wt. but in the preferred embodiment, the range may be between 10% and 20% wt./wt. The formulation may also contain an emulsifier, a rheological additive, a polar additive for gellation and other additives such as non-ionic surfactants and antioxidants such that the solid allicin powder concentrate is incorporated as a homogenous suspension and the resultant suspension concentrate formulation is easily flowable, pourable, forms instant emulsion upon addition to water and the mixture is either easily sprayed through conventional spray equipment or applied through irrigation or other means.

In the preferred embodiment the emulsifier is a polyol fatty acid ester and a polyethoxylated derivative thereof. The concentration of the emulsifier may be in the range of 3 to 12% wt./wt. and more preferably around 5% wt./wt. of the formulation. The formulation may also contain up to 2% polysorbate 20 and more preferably 0.5% wt./wt. The preferred rheological additive is organically modified hectorite clay, which may range between 0.8 to 2% wt./wt. of the formulation and more preferably around 1.6% wt./wt. The preferred polar additive for developing proper gellation is propylene carbonate, although other additives such as ethanol/water (95:5 ratio) or methanol/water (95:5 ratio) may also be used. The concentration of the preferred polar additive may range from 0.5 to 3% wt./wt. and more preferably is about 1% wt./wt. of the formulation. The polar additive acts as a wedge to open up the clay platelets in order to make them capable of developing maximum gellation. The formulation may also contain other suitable additives such as an antioxidant and/or other surfactants for soil penetration of the active ingredients.

In another embodiment, the invention provides a method of protecting a plant from at least one pest or pathogen comprising application to the plant an effective amount of the claimed formulations. In one embodiment, the pest or pathogen may be a nematode.

In one embodiment, the target crop protected from nematode damage may be any vegetable, fruit trees, vines and row crop of economic importance. It may also be turf, flowerbeds, potted plants or an ornamental or forestry nursery crop.

In one embodiment, the application of the formulation is performed by mixing it in a suitable amount of water or other compatible liquid carrier and applying it to the target crop or soil either by spray equipment or through irrigation equipment. The product may also be sprayed onto the seedling or seeding beds and incorporated into the soil or growing medium.

These representative embodiments are in no way limiting and are described solely to illustrate some aspects of the invention.

The following examples are offered by way of illustration only and not by way of limitation.

EXAMPLE 1

TABLE 1

Examples of three prototype formulation compositions evaluated for nematicidal activity

| No. | Component | % wt./wt. | % wt./wt. | % wt./wt. |
|---|---|---|---|---|
|  | Formulation ID and Ratio of | 1-A | 1-B | 1-C |
|  | Cinnamaldehyde:Allicin | 5:1 | 7:1 | 10:1 |
| 1 | Isopar M (Isoparaffinic Oil) | 22.4 | 18.0 | 11.3 |
| 2 | Soy oil Methyl Ester | 32.7 | 32.7 | 32.7 |
| 3 | Cinnamaldehyde, 98.5% | 11.1 | 15.5 | 22.2 |
| 4 | Allicin (10%) | 21.8 | 21.8 | 21.8 |
| 5 | Organophilic Hectorite Clay | 1.1 | 1.1 | 1.1 |
| 6 | Polyol fatty acid esters and polyethoxylated derivatives there of: | 9.8 | 9.8 | 9.8 |
| 7 | Polysorbate 20 (Tween 20) | 1.1 | 1.1 | 1.1 |
|  | Total | 100 | 100 | 100 |

Method of Preparation of Gel Concentrate for use in Prototype Formulations as Detailed in Table 1:

A gel concentrate is first prepared by combining, under high shear, soybean oil (76 parts), organically modified hectorite clay (12 parts) and emulsifier polyol fatty acid esters and its derivatives (12 parts).

Method of Preparation of Cinnamaldehyde+Allicin (10%) Prototype Formulations as Detailed in Table 1:

Isoparaffinic fluid Isopar M is first charged to a vessel of suitable size and equipped with a variable speed mixer/agitator. The required amount of gel concentrate is then added and mixed until it is homogeneously dispersed. Cinnamaldehyde dissolved in Soy oil Methyl Ester is charged and mixed. Emulsifier and polysorbate are added and propeller mixed. Allicin (10%) is slowly charged while mixing under high shear. Mixing is continued until garlic extract is homogeneously dispersed.

EXAMPLE 2

TABLE 2

Examples of three preferred formulations showing synergistic activity against root knot nematodes.

| No. | Component | % wt./wt. | % wt./wt. | % wt./wt. |
|---|---|---|---|---|
|  | Formulation ID and Ratio of | 2-A | 2-B | 2-C |
|  | Cinnamaldehyde:Allicin | 5:1 | 7:1 | 10:1 |
| 1 | Soybean Oil | 61.74 | 57.74 | 51.54 |
| 2 | Cinnamaldehyde, 98.5% | 10.20 | 14.20 | 20.40 |
| 3 | Allicin (10%) | 20.00 | 20.00 | 20.00 |
| 4 | Organophilic Hectorite Clay | 1.60 | 1.60 | 1.60 |
| 5 | Polyol fatty acid esters and polyethoxylated derivatives there of: | 5.00 | 5.00 | 5.00 |
| 6 | Propylene Carbonate Jeffsol AG1555 (Huntsman Corp.) | 0.96 | 0.96 | 0.96 |
| 7 | Polysorbate 20 (Tween 20) | 0.50 | 0.50 | 0.50 |
|  | Total | 100.0 | 100.0 | 100.0 |

EXAMPLE 3

TABLE 3

Example of a preferred formulation showing synergistic activity against root knot nematodes.

| No. | Component | % wt./wt. |
|---|---|---|
|  | Formulation ID and Ratio of Cinnamaldehyde:Allicin | 7:1 |
| 1 | Soybean Oil | 49.78 |
| 2 | Cinnamaldehyde, 98.5% | 17.8 |
| 3 | Allicin (10%) | 25.00 |
| 4 | Organophilic Hectorite Clay | 1.20 |
| 5 | Polyol fatty acid esters and polyethoxylated derivatives there of: | 5.00 |
| 6 | Propylene Carbonate Jeffsol AG1555 (Huntsman Corp.) | 0.72 |
| 7 | Polysorbate 20 (Tween 20) | 0.50 |
|  | Total | 100.0 |

Method of Preparation of Gel Concentrate for use in Preferred Formulations Detailed in Table 2 and 3:

A gel concentrate is first prepared by combining, under high shear, soybean oil (87 parts), organically modified hectorite clay (5 parts), emulsifier blend containing Polyol fatty acid esters and polyethoxylated derivatives there of (5 parts) and propylene carbonate (3 parts). The amount of organophilic hectorite clay in the gel concentrate may range between 2 to 10% wt./wt. Similarly, the amount of propylene carbonate or other polar additives may range from 0.5% to 5% wt./wt.

Method of preparation of cinnamaldehyde allicin (10%) preferred formulations as detailed in Table 2 and 3:

Soybean oil is first charged to a stainless steel vessel of suitable size and equipped with a variable speed mixer/agitator. While mixing, cinnamaldehyde is charged and mixed to dissolve. The required amount of gel concentrate is then added and mixed until it is homogeneously dispersed. Allicin (10%) is slowly charged and mixed until it is homogeneously dispersed.

Emulsifier and Polysorbate 20 are charged and mixed until all contents are homogeneously dispersed. The suspension thus formed is passed through a 149 micron opening sieve.

EXAMPLE 4

TABLE 4

Examples of two preferred formulations that may be prepared by the procedure of Example 3.

| No. | Component | % wt./wt. | % wt./wt. |
|---|---|---|---|
|  | Formulation ID and Ratio of Cinnamaldehyde:Allicin | -A 15:1 | -B 20:1 |
| 1 | Soybean Oil | 41.39 | 31.09 |
| 2 | Cinnamaldehyde, 98.5% | 30.46 | 40.61 |
| 3 | Allicin (10%) | 20.00 | 20.00 |
| 4 | Organophilic Hectorite Clay | 1.65 | 1.70 |
| 5 | Polyol fatty acid esters and polyethoxylated derivatives there of: | 5.00 | 5.00 |
| 6 | Propylene Carbonate Jeffsol AG1555 (Huntsman Corp.) | 1.00 | 1.10 |
| 7 | Polysorbate 20 (Tween 20) | 0.50 | 0.50 |
|  | Total | 100.0 | 100.0 |

EXAMPLE 5

Efficacy Evaluation of Formulation Compositions Containing Cinnamaldehyde and Allicin (10%) at 5:1, 7:1, and 10:1 ratios.

Procedure for Greenhouse pot Tests:

2"×2" plastic pots are filled with 140 to 150 g of plant growth medium that is made up of non-pasteurized sand and soil at 2:1 ratio. Three cucumber seeds (variety Straight Eight; in the case of tomatoes, variety Rutgers) are planted at uniform depth and watered. Upon emergence, two uniform seedlings are allowed to grow in each pot by removing the third seedling. Seedlings are selected when the first true leaf is emerged, generally 5 to 7 days after planting. Each pot is treated with test material diluted in 25 mL of water that is just sufficient to wet the soil but not drip. Except for untreated control, all test pots are inoculated with about 800 second stage juveniles of Root Knot Nematodes (*Meloidogyne incognita*). Plants are watered as needed. Twelve to fourteen days after the pots are inoculated, the plants are carefully removed from the pots, the roots are gently washed free of soil and placed on paper towels, and data on fresh weight of shoots, roots, number of galls/treatment and/or per gram of root are taken. Roots are also rated for galling on a scale of 0 to 9 where in zero represents roots with out exhibiting galls and 9 represents roots exhibiting heavy galling.

TABLE 5

Efficacy evaluations of three prototype formulation compositions as detailed in Table 1.

| No. | Treatment Detail | Average gall rating (0-9) | % gall reduction in relation to M.i Control |
|---|---|---|---|
| 1 | Untreated Control | 0 | 0 |
| 2 | M.i. (nematode) control | 8.25 | 0 |
| 3 | Cinnamaldehyde at 300 ppm (a.i. basis) (50% Cinnamaldehyde formulation (VBC-90009) | 5.50 | 33.3 |
| 4 | Allicin at 300 ppm mixed in water | 2.25 | 72.7 |
| 5 | Cinnamaldehyde (250 ppm):Allicin (50 ppm) - 5:1 ratio (Table 1.1-A) | 4.75 | 42.2 |
| 6 | Cinnamaldehyde (262.5 ppm):Allicin (37.5 ppm) - 7:1 ratio (Table 1.1-B) | 4.00 | 51.5 |
| 7 | Cinnamaldehyde (272.7 ppm):Allicin (27.3 ppm) - 10:1 ratio (Table 1.1-C) | 2.00 | 75.8 |

Data for gall rating and % gall reduction as shown in Table 5 reveal that allicin at 300 ppm is more effective than cinnamaldehyde at a similar concentration of 300 ppm. Among the ratios tested, the 10:1 ratio containing 272.7 ppm of cinnamaldehyde and 27.3 ppm allicin gives similar gall reduction as allicin alone at 300 ppm.

TABLE 6

Efficacy Evaluations of three preferred formulations as described in Table 2 on cucumber root gall rating.

| No. | Treatment Detail | Average gall rating (0-9) | % gall reduction in relation to M.i Control |
|---|---|---|---|
| 1 | Untreated Control | 0 | 0 |
| 2 | M.i. (nematode) control | 9 | 0 |
| 3 | Cinnamaldehyde at 300 ppm (a.i. basis) (Composition same as in Table 2.2-C minus garlic extract) | 7.25 | 19.4 |

TABLE 6-continued

Efficacy Evaluations of three preferred formulations as described in Table 2 on cucumber root gall rating.

| No. | Treatment Detail | Average gall rating (0-9) | % gall reduction in relation to M.i Control |
|---|---|---|---|
| 4 | Allicin at 300 ppm (Composition same as in Table 2.2-C minus cinnamaldehyde) | 5.25 | 41.7 |
| 5 | Cinnamaldehyde (250 ppm):Allicin (50 ppm) - 5:1 ratio (Table 2.2-A) | 0.5 | 94.4 |
| 6 | Cinnamaldehyde (262.5 ppm):Allicin (37.5 ppm) - 7:1 ratio (Table 2.2-B) | 0.5 | 94.4 |
| 7 | Cinnamaldehyde (272.7 ppm):Allicin (27.3 ppm) - 10:1 ratio (Table 2.2-C) | 0 | 100.0 |

The data shown in Table 6 clearly demonstrated a synergistic response for all the three formulations by substantially reducing or almost eliminating galls caused by root knot nematodes. The data further reveal that the compositions detailed in Table 2 are more preferred than those detailed in Table 1. In the above example, this invention has a practical implication in that these compositions are more economical in addition to their potential in replacing environmentally hazardous synthetic nematicides such as DBCP and EDB.

TABLE 7

Efficacy Evaluations of most preferred formulation as described in Table 3 on cucumber root gall rating using unpasteurized soil, and standard greenhouse bioassay (average of three tests)

| No. | Treatment Detail | Average gall rating (0-9) | % gall reduction in relation to M.i Control |
|---|---|---|---|
| 1 | Untreated Control | 0 | 0 |
| 2 | M.i. (nematode) control | 9 | 0 |
| 3 | Composition of Example 3 (Cinnamaldehyde:Allicin 7:1) at 300 ppm total A.I. | 0 | 98.0 |

Standard Greenhouse Bioassay:

The bioassay is conducted by using Cucumber seedlings grown in 2" pots. The test material is diluted to the appropriate concentration and applied in a volume of 25 ml/pot. Pots are monitored for 10-12 days and are harvested afterwards. After harvest, data on seedling fresh weight and gall rating are collected.

The data in the Table 7 clearly demonstrate the ability of the composition described in Example 3 to eliminate root galling at the tested rate.

TABLE 8

Efficacy Evaluations of the formulation described in Table 3 on Tomato root gall rating using mother soil (highly infected soil with eggs and juveniles).

| No. | Treatment Detail | Average gall rating (0-9) | % gall reduction in relation to M.i Control |
|---|---|---|---|
| 1 | Untreated Control | 0 | 0 |
| 2 | Mother soil | 6.9 | 0 |
| 4 | Composition of Example 3 (Cinnamaldehyde:Allicin 7:1) at 5000 PPM total A.I. | 0.0 | 100 |
| 5 | Composition of Example 3 (Cinnamaldehyde:Allicin 7:1) at 3000 PPM total A.I. | 0.3 | 96 |
| 6 | Composition of Example 3 (Cinnamaldehyde:Allicin 7:1) at 2000 PPM total A.I. | 0.0 | 100 |
| 7 | Composition of Example 3 (Cinnamaldehyde:Allicin 7:1) at 1500 PPM total A.I. | 2.0 | 71 |
| 8 | Composition of Example 3 (Cinnamaldehyde:Allicin 7:1) at 1000 PPM total A.I. | 4.5 | 35 |
| 9 | Composition of Example 3 (Cinnamaldehyde:Allicin 7:1) at 500 PPM total A.I. | 5.8 | 16 |

Mother soil is defined as soil highly infected soil with root knot nematode (*Meloidogyne incognita*) eggs and juveniles. This experiment assesses the performance of the formulation of Example 3 under extreme soil nematode infestation. Rates required to achieve comparable results under field conditions could actually be lower than those in Table 8.

Methods of Testing in Mother Soil (Pot Test):

4" pots are filled with mother soil at 500 g/pot. The test material is diluted to the appropriate concentration and applied in a volume of 90 ml to each pot. After the initial application, pots are wrapped with polyethylene film (saran wrap). One week after the initial application, tomato seedlings are transplanted into each pot and then monitored for two weeks. At harvest, fresh weight and gall control is assessed for all plants.

The data in Table 8 show that the formulation of Example 3 effectively controls root galling in highly infected soil.

TABLE 9

Field evaluation of the formulation described in Example 3 for nematode control on squash

| No. | Treatment Detail | Average root gall rating (0-10) |
|---|---|---|
| 1 | Untreated | 9.71 |
| 2 | Composition of Example 3 (Cinnamaldehyde:Allicin 7:1) at 1.15 gal/A preplant | 6.24 |
| 3 | Composition of Example 3 (Cinnamaldehyde:Allicin 7:1) at 1.15 gal/A preplant + 21 day after planting (total of 2 applications) | 7.21 |
| 4 | Composition of Example 3 (Cinnamaldehyde:Allicin 7:1) at 1.15 gal/A preplant + 21 days after planting + 35 days after planting (total of 3 applications) | 7.37 |
| 5 | Composition of Example 3 (Cinnamaldehyde:Allicin 7:1) at 2.3 gal/A preplant | 5.27 |
| 6 | Composition of Example 3 (Cinnamaldehyde:Allicin 7:1) at 2.3 gal/A preplant + 21 days after planting (total of 2 applications) | 4.49 |
| 7 | Composition of Example 3 (Cinnamaldehyde:Allicin 7:1) 2.3 gal/A preplant + 21 days after planting + 35 days after planting (total of 3 applications) | 4.86 |
| 8 | Composition of Example 3 (Cinnamaldehyde:Allicin 7:1) 3.45 gal/A preplant | 4.76 |

TABLE 9-continued

Field evaluation of the formulation described
in Example 3 for nematode control on squash

| No. | Treatment Detail | Average root gall rating (0-10) |
|---|---|---|
| 9 | Composition of Example 3 (Cinnamaldehyde:Allicin 7:1) 3.45 gal/A preplant + 21 days after planting (total of 2 applications) | 8.58 |
| 10 | Composition of Example 3 (Cinnamaldehyde:Allicin 7:1) 3.45 gal/A preplant + 21 days after planting + 35 days after planting (total of 3 applications) | 4.32 |
| 11 | Vydate (2 pints/A) preplant (Chemical Control) | 5.97 |

Data for gall rating as shown in Table 9 reveal that the formulation of Example 3 effectively controls galling caused by root knot nematodes. The data show that this composition has the potential to replace environmentally hazardous synthetic nematicides.

The invention claimed is:

1. A formulation suitable for agricultural use consisting of cinnamaldehyde, allicin (10%), soybean oil, an emulsifier, an organophilic hectorite clay, propylene carbonate and a nonionic surfactant.

2. The formulation of claim 1, wherein said emulsifier is a polyol fatty acid ester or polyethoxylated derivative thereof.

3. The formulation of claim 1, wherein cinnamaldehyde plus allicin (10%) comprise about 30% to 50.0% wt./wt. of the total formulation, soybean oil comprises about 50 to 80% wt./wt. of the total formulation, emulsifier comprises about 3 to 12% wt./wt. of the total formulation, organophillic hectorite clay comprises 0.8 to 2% wt./wt., polar additive propylene carbonate comprises about 0.5 to 3% wt./wt., and nonionic surfactant comprises about 0.5 to 2% wt./wt.

4. The formulation of claim 3, wherein the ratio of cinnamaldehyde to allicin ranges from 1:1 to 20:1.

5. The formulation of claim 1, wherein, the cinnamaldehyde concentration in the formulation ranges from 10 to 20% wt./wt.

6. The formulation of claim 3, wherein the allicin (10%) in the formulation ranges from 10 to 40% wt./wt. of the total formulation.

7. A method of protecting a plant from nematodes comprising applying to the plant or soil an effective amount of the formulation of claim 3.

8. The method of claim 7, wherein the formulation is applied either prior to planting or following planting, neat or diluted in water or other agricultural carriers to the plant or soil either by spray equipment or by irrigation equipment.

9. The method of claim 7, wherein the formulation is tank-mixed with pesticides and/or fertilizer solutions for enhanced pesticidal activity or for economic reasons.

* * * * *